US00PP15308P2

(12) United States Plant Patent
Sjulin et al.

(10) Patent No.: US PP15,308 P2
(45) Date of Patent: Nov. 9, 2004

(54) STRAWBERRY PLANT NAMED 'DRISCOLL CORONATION'

(50) Latin Name: *Fragaria×ananassa*
Varietal Denomination: Driscoll Coronation

(75) Inventors: Thomas M. Sjulin, Aromas, CA (US); Joseph T. DeRuse, Almeria (ES); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 10/619,692

(22) Filed: Jul. 15, 2003

(51) Int. Cl.[7] ..... A01H 5/00
(52) U.S. Cl. ..... Plt./209
(58) Field of Search ..... Plt./209, 208

*Primary Examiner*—Anne Marie Grunberg
*Assistant Examiner*—June Hwu
(74) *Attorney, Agent, or Firm*—Jones Day

(57) ABSTRACT

This invention relates to a new and distinct variety of strawberry named 'Driscoll Coronation.' The variety is similar to the varieties 'Driscoll Camarillo' and 'Driscoll Jubilee.' The variety is distinguished from 'Driscoll Camarillo' and 'Driscoll Jubilee', in particular, by a whitish internal fruit color, a flat habit, a strong leaf glossiness, inflorescence level in relation to the foliage, weak fruit acidity, and medium adherence of fruit to the clayx.

3 Drawing Sheets

Latin name of the genus and species of the plant claimed: The variety is botanically identified as *Fragaria×ananassa*.

Variety denomination: The strawberry variety denomination is 'Driscoll Coronation'.

1. BACKGROUND OF THE INVENTION

The new variety originated as a result of a controlled cross between the strawberry plants 'Marathon' (U.S. Plant Pat. No. PP12,817) and '38A237' (unpatented variety) in an ongoing breeding program, and was discovered as a seedling in Kent, England in 1999. The original seedling of the new cultivar was asexually propagated by stolons in a Nursery in Kent, England. Propagules were transplanted to a controlled breeding plot in Monterey. Calif, where the variety was identified and selected for further evaluation. 'Driscoll Coronation' was subsequent asexually propagated and underwent further testing in Monterey, Calif. for one year. This propagation and testing has demonstrated that the combination of traits disclosed herein which characterize the new variety are fixed and retained true to type through successive generation of asexual reproduction.

2. SUMMARY OF THE INVENTION

The present invention relates to a new and distinct variety of strawberry named 'Driscoll Coronation.' The variety is botanically identified as *Fragaria×ananassa.* The new variety is distinguished from other varieties by a number of characteristics as set forth in Tables 1–4.

3. COMPARISON TO SIMILAR VARIETIES

The varieties which we believe to be similar to 'Driscoll Coronation' from those known to us are 'Driscoll Camarillo' (U.S. Plant Pat. No. 04,771) and 'Driscoll Jubilee' (U.S. Plant patent application Ser. No. 10/619,689). There are several characteristics of the new variety that are different from, or not possessed by 'Driscoll Camarillo' and 'Driscoll Jubilee.' The new variety is distinguished from 'Driscoll Camarillo' and 'Driscoll Jubilee' by having a flat habit, a strong leaf glossiness, inflorescence level in relation to the foliage, weak fruit acidity, and medium adherence of fruit to the calyx. The internal fruit color of 'Driscoll Coronation' is whitish. In contrast, the internal fruit color of 'Driscoll Camarillo' and 'Driscoll Jubilee' comprises a white color interspersed in a striped manner among the orange-red or red color described for each variety. Each color described for the internal fruit color of 'Driscoll Camarillo' and 'Driscoll Jubilee' is individually present in the internal fruit tissues.

'Driscoll Coronation' is distinguished from its maternal parent 'Marathon' by its smaller fruit size, lighter internal color, and its fully everbearing habit. 'Driscoll Coronation' is distinguished from its paternal parent '38A237' by its larger average fruit size, paler internal fruit color, and broader fruit shape.

4. BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

5. DESCRIPTION OF THE NEW VARIETY

Figure 1:
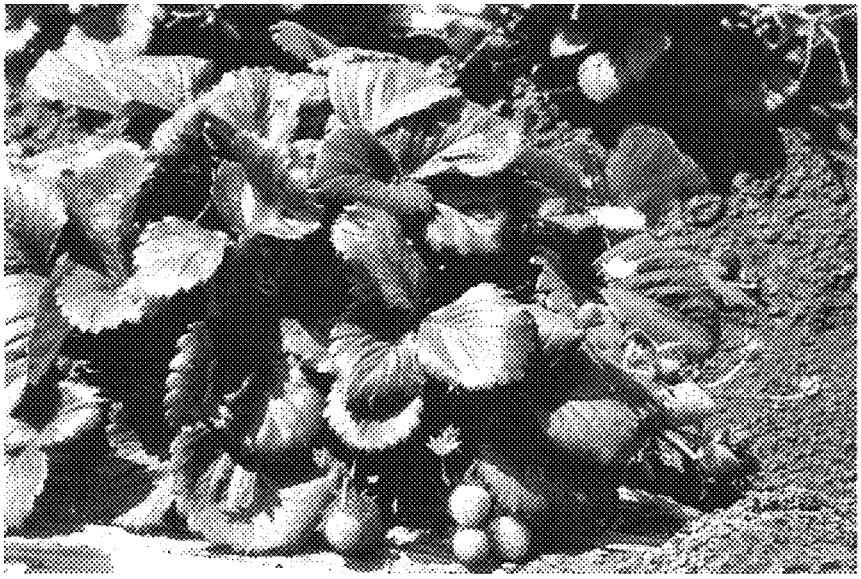
FIG. 1 shows the whole the plant.
Figure 2:
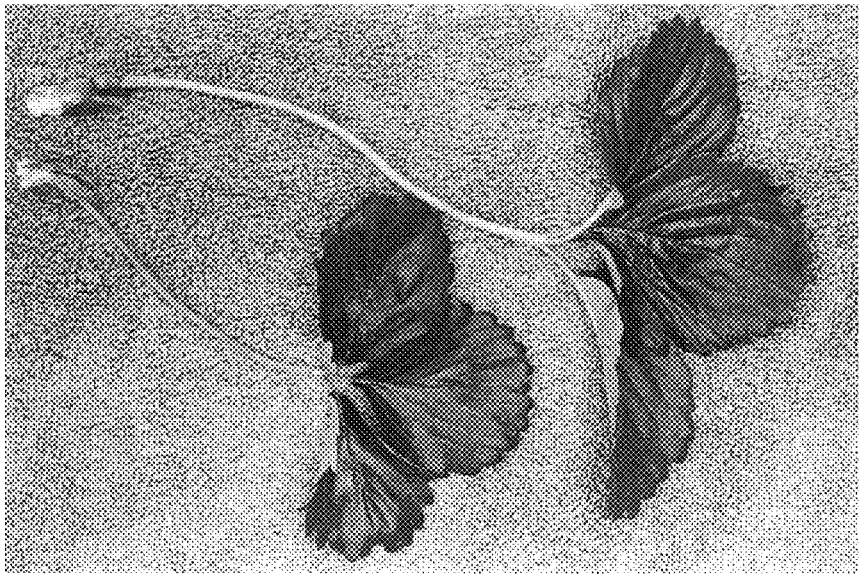
FIG. 2 shows the upper side of the leaves of the plant
Figure 3:
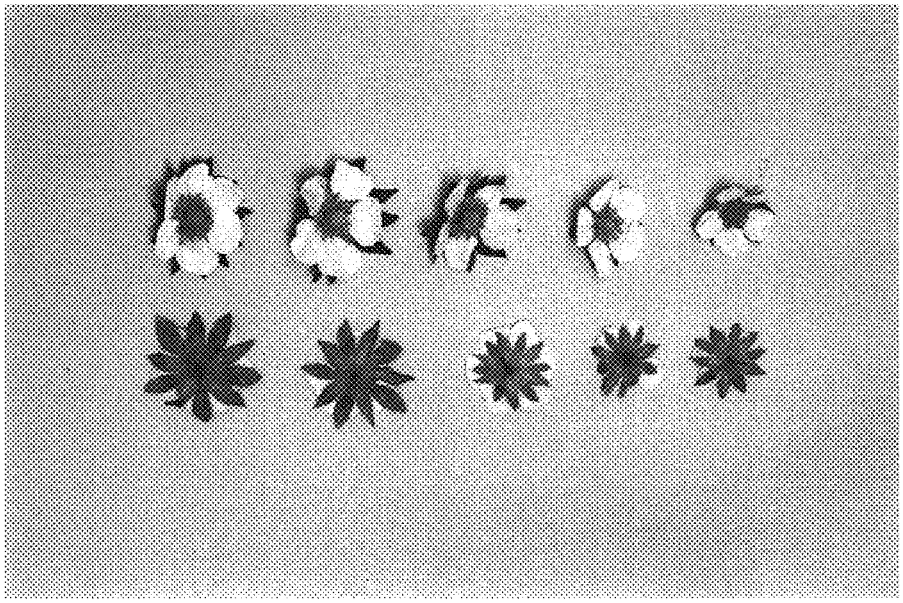
FIG. 3 shows the under side and underside of the flowers.
Figure 4:
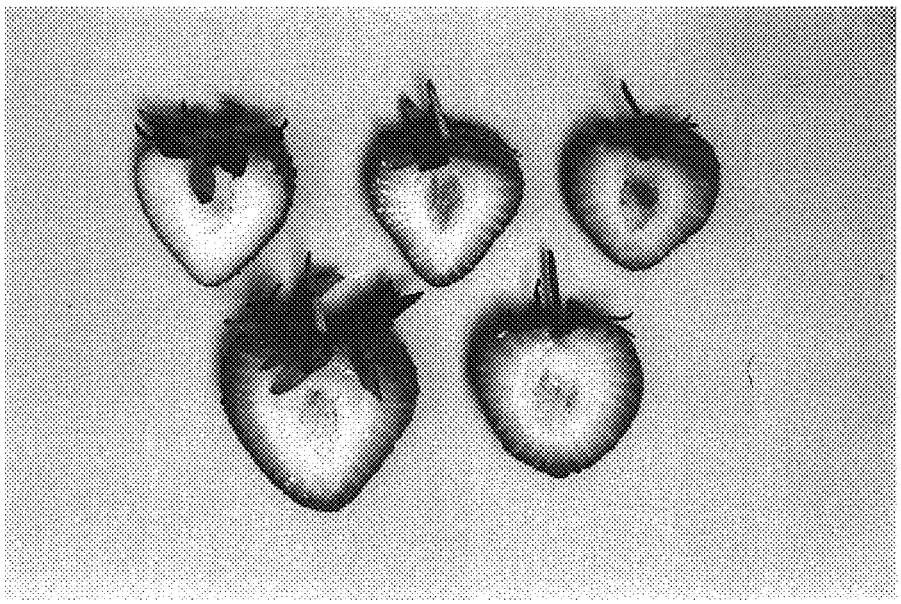
FIG. 4 shows the fruit in longitudinal cross-section.
Figure 5:
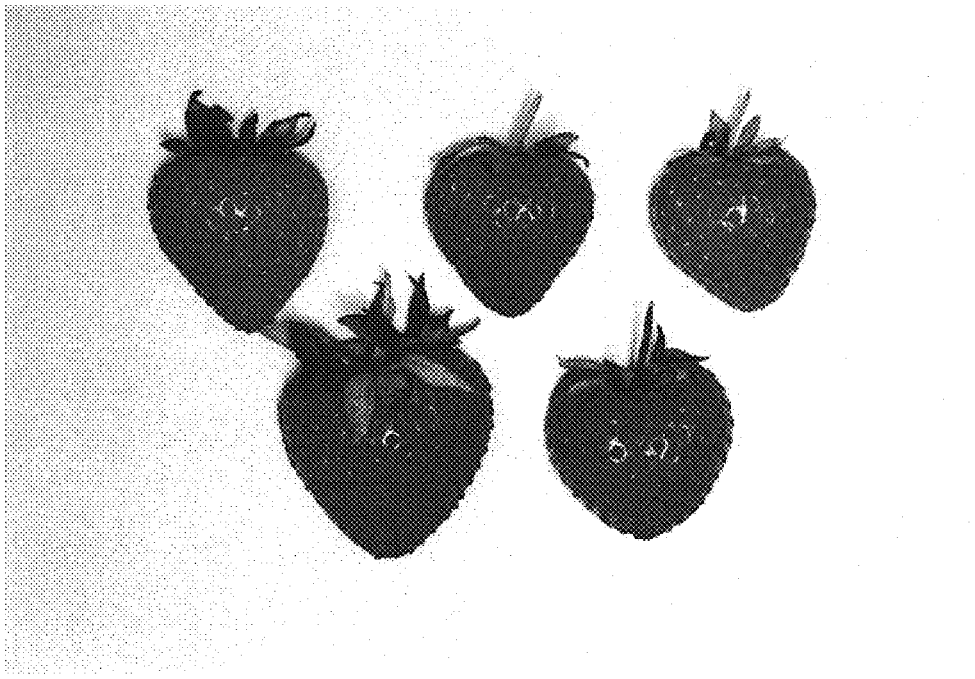
FIG. 5 shows a close-up of the fruit.

The following detailed description of the new variety is based upon observations taken of plants and fruit grown in Monterey County, Calif., U.S.A. This description is in accordance with UPOV terminology. Observations of Driscoll Coronation, 'Driscoll Camarillo,' and 'Driscoll Jubilee' were taken in side by side comparison in the year 2002. Plants for observation were harvested from a low elevation nursery in Tehama County, Calif. in December 2001, and held in refrigerated storage until planting in Monterey County in March 2002. Plants were grown in raised beds of soil under conditions typical of commercial strawberry production along the central coat of California. Fruits were harvested twice weekly for yield determination from May to October 2002. Measurements of plant, flower, and fruit characteristics were made in August 2002, approximately 5 months after planting. Color designations, color descriptions, and other phenotypical descriptions may deviate from the state values and descriptions depending upon variation in environmental, seasonal, climatic and cultural conditions. Colors are described and the most similar color designations are provided from The Royal Horticultural Society (R.H.S.) Colour Chart.

5.1 PROPAGATION

The new variety is principally propagated by way of stolons. Although propagation by stolons is presently preferred, other known methods of propagating strawberry plants may be employed.

5.2 CHARACTERISTICS OF THE NEW VARIETY

Information on the new variety is presented in Tables 1, 2, 3 and 4. In the tables, the flowers described are secondary flowers except where indicated. The fruit described is the secondary fruit on five month old plants. Fruit and flower measurements are an average of both primary and secondary fruit and flowers.

Table 1 provides information on the plant and fruit characteristics of the new variety 'Driscoll Coronation' compared with characteristics of 'Driscoll Camarillo' and 'Driscoll Jubilee.' Table 2 provides additional information of the plant and fruit characteristics of the new variety 'Driscoll Coronation' compared with characteristics of the varieties 'Driscoll Camarillo' and 'Driscoll Jubilee.' Table 3 provides reactions of the new variety to stresses, pests and diseases compared with reactions of the varieties 'Driscoll Camarillo' and 'Driscoll Jubilee.' Table 4 provides isozyme characteristics of the new variety as compared to that of the varieties 'Driscoll Camarillo' and 'Driscoll Jubilee.'

TABLE 1

QUANTITATIVE COMPARISON OF 'DRISCOLL CORONATION', 'DRISCOLL CAMARILLO,' AND 'DRISCOLL JUBILEE'

| | 'Driscoll Coronation' | 'Driscoll Camarillo' | 'Driscoll Jubilee' |
|---|---|---|---|
| Plant Characteristics | | | |
| Height of plant (cm) | 17.0 | 20.5 | 18.3 |
| Spread of plant (cm) | 33.2 | 39.4 | 30.7 |
| Number of crowns | 3.7 | 3.0 | 3.5 |
| Leaf Characteristics | | | |
| Terminal leaflet length (cm) | 7.9 | 8.4 | 6.9 |
| Terminal leaflet width (cm) | 7.4 | 8.5 | 6.7 |
| Terminal leaflet length/width ratio | 1.07 | 0.99 | 1.04 |
| # Teeth/terminal leaflet | 24.3 | 27.0 | 20.1 |
| Color of upper side | 147A dark green | 147A dark green | 147A dark green |
| Color of under side | 139C light to medium green | 147C light green | 138B light to medium green |
| Petiole length (cm) | 16.2 | 16.8 | 15.8 |
| Petiole color | 145A | 145A | 145A |

TABLE 1-continued

QUANTITATIVE COMPARISON OF 'DRISCOLL CORONATION', 'DRISCOLL CAMARILLO,' AND 'DRISCOLL JUBILEE'

| | 'Driscoll Coronation' | 'Driscoll Camarillo' | 'Driscoll Jubilee' |
|---|---|---|---|
| Bract frequency | 25% typically double | 67% typically double | 42% typically double |
| Stipule length (cm) | 3.3 | 4.0 | 3.1 |
| Stipule width (cm) | 0.8 | 1.0 | 1.0 |
| Flower Characteristics | | | |
| Petal length (cm) | 0.96 | 1.13 | 1.12 |
| Petal width (cm) | 0.93 | 1.29 | 1.17 |
| Petal length/width Ratio | 1.03 | 0.88 | 0.96 |
| Flower diameter (cm) | 2.55 | 3.17 | 2.92 |
| Calyx diameter (cm) | 2.51 | 3.09 | 2.65 |
| Average Fruiting truss length (cm) | 24.2 | 33.2 | 27.7 |
| Petal color (cm) | 155C | 155C | 155C |
| Fruit Characteristics | | | |
| Fruit length (cm) | 3.9 | 3.8 | 3.8 |
| Fruit width (cm) | 3.9 | 3.9 | 3.4 |
| Fruit length/width Ratio | 0.99 | 0.97 | 1.10 |
| Average berry weight (g) | 20.0 | 20.7 | 19.8 |
| External color | 45B red | 42A red | 45A red |
| Internal color | 159D whitish | 33A–155C orange red and white | 43A–155B red and white |
| Achene coloration | 184A to 8B | 184B to 4B | 184A to 4A |
| Yield (g/plant) | 850 | 1200 | 600 |

TABLE 2

QUALITATIVE COMPARISON OF 'DRISCOLL CORONATION', 'DRISCOLL CAMARILLO,' AND 'DRISCOLL JUBILEE'

| | 'Driscoll Coronation' | 'Driscoll Camarillo' | 'Driscoll Jubilee' |
|---|---|---|---|
| Plant | | | |
| Habit | flat | flat globose | flat globose |
| Density | open | open | open to medium |
| Vigor | weak to medium | medium to strong | weak to medium |
| Leaf | | | |
| Shape in cross section | slightly concave to flat | concave | slightly concave to flat |
| Interveinal blistering | medium | strong | strong |
| Glossiness | strong | medium to strong | medium |
| Number of leaflets | three only | three only | three only |
| Terminal leaflet margin profile | revolute | revolute | revolute |
| Terminal leaflet shape of base | obtuse | rounded | acute |
| Terminal leaflet shape of teeth | obtuse | rounded | Rounded |
| Stipule pubescence | sparse | medium | sparse to medium |
| Petiole pubescence | very sparse to sparse | sparse | very sparse |
| Petiole pose of hairs | outwards | upwards to outward | outwards to downwards |
| Stolon | | | |
| Amount | few to medium | medium | Medium |

TABLE 2-continued

QUALITATIVE COMPARISON OF 'DRISCOLL CORONATION', 'DRISCOLL CAMARILLO,' AND 'DRISCOLL JUBILEE'

| | 'Driscoll Coronation' | 'Driscoll Camarillo' | 'Driscoll Jubilee' |
|---|---|---|---|
| Anthocyanin coloration | medium | medium | Medium |
| Thickness | medium | thick | thin to medium |
| Pubescence | medium | medium | sparse to medium |
| Inflorescence | | | |
| Position relative to foliage | level | above | beneath |
| Diameter of calyx relative to corolla on secondary flowers | smaller to same size | smaller to same size | smaller to same size |
| Diameter of inner calyx relative to outer on secondary flowers | smaller | same size | smaller |
| Spacing of petals | touching | overlapping | touching to overlapping |
| Fruiting Truss | | | |
| Attitude at first picking | prostrate | semi-erect to prostrate | semi-erect |
| Fruit | | | |
| Predominant shape | chordate | chordate | conical |
| Difference in shapes between primary and secondary fruits | slight to moderate | slight to moderate | very slight to slight |
| Band without achenes | very narrow | very narrow | very narrow |
| Unevenness of surface | very weak to weak | weak to medium | very weak |
| Evenness of color uneven | slightly uneven to even | Even | slightly uneven |
| Glossiness | strong | Strong | strong |
| Insertion of achenes | level | below to level | level to above |
| Insertion of calyx | in a basin | in a basin | in a basin to level |
| Pose of the calyx segments | spreading | spreading to reflexed | spreading |
| Size of calyx in relation to fruit on secondary fruit | same size to larger | Smaller | smaller to same size |
| Adherence of calyx | medium | strong | strong |
| Firmness of flesh | medium | firm | medium to firm |
| Evenness of flesh color | even | slightly uneven | slightly uneven |
| Distribution of flesh color | central | marginal and central | marginal and central |
| Hollow center size | small to medium | absent to small | absent to small |
| Sweetness | strong | medium | medium to strong |
| Texture when tasted | fine | medium | medium |
| Acidity | weak | Medium | medium |
| Time of Flowering | medium | medium | medium |
| Type of Bearing | fully everbearing | fully everbearing | fully everbearing |

5.3 REACTION TO STRESS, PESTS, AND DISEASE

TABLE 3

REACTIONS TO STRESS PESTS AND DISEASES FOR 'DRISCOLL CORONATION', 'DRISCOLL CAMARILLO,' AND 'DRISCOLL JUBILEE'

| | 'Driscoll Coronation' | 'Driscoll Camarillo' | 'Driscoll Jubilee' |
|---|---|---|---|
| Reaction to Stress | | | |
| high pH | moderately resistant | moderately resistant | moderately resistant |
| high soil salt levels | moderately susceptible | moderately resistant | moderately susceptible |
| Reaction to Pests | | | |
| *Tetranychus urticae* | moderately susceptible | moderately susceptible | moderately susceptible |
| *Lygus hesperus* | susceptible | susceptible | susceptible |
| Reaction To Diseases | | | |
| Botrytis fruit rot | moderately susceptible to moderately resistant | moderately susceptible to moderately resistant | moderately susceptible to moderately resistant |
| Powdery mildew | moderately susceptible | susceptible to highly susceptible | susceptible |
| Verticillium wilt | moderately susceptible | moderately susceptible | moderately resistant |

5.4 ISOZYME ANALYSIS

In addition to the morphological description above, the new cultivar 'Driscoll Coronation' has been analyzed to obtain an indication of its genetic makeup to provide further means for identifying the new variety and distinguishing it from other somewhat similar and/or related strawberry varieties. Specifically, leaf samples of 'Driscoll Coronation', 'Driscoll Camarillo' and 'Driscoll Jubilee' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL CORONATION', 'DRISCOLL CAMARILLO,' AND 'DRISCOLL JUBILEE'

| Locus | 'Driscoll Camarillo' | 'Driscoll Coronation' | 'Driscoll Jubilee' |
|---|---|---|---|
| PGI | A2 | A3 | A1 |
| LAP | B3 | B3 | B3 |
| PGM | C4 | C4 | C4 |

What is claimed is:

1. A new and distinct variety of strawberry plant, substantially as shown and described.

* * * * *